(12) United States Patent
Makimura et al.

(10) Patent No.: US 11,753,689 B2
(45) Date of Patent: Sep. 12, 2023

(54) **PRIMER SET FOR USE IN DETECTION OF *CANDIDA AURIS*, *CANDIDA AURIS* DETECTION KIT, AND *CANDIDA AURIS* DETECTION METHOD**

(71) Applicant: TEIKYO UNIVERSITY, Tokyo (JP)

(72) Inventors: Koichi Makimura, Tokyo (JP); Mikachi Yamamoto, Tokyo (JP); Mohamed Mahdi Alshahni, Tokyo (JP)

(73) Assignee: TEIKYO UNIVERSITY, Tokyo (JP)

( * ) Notice: Subject to any disclaimer, the term of this patent is extended or adjusted under 35 U.S.C. 154(b) by 31 days.

(21) Appl. No.: 17/048,244

(22) PCT Filed: Apr. 25, 2019

(86) PCT No.: PCT/JP2019/017606
§ 371 (c)(1),
(2) Date: Oct. 16, 2020

(87) PCT Pub. No.: WO2019/208691
PCT Pub. Date: Oct. 31, 2019

(65) Prior Publication Data
US 2021/0164058 A1  Jun. 3, 2021

(30) Foreign Application Priority Data

Apr. 27, 2018 (JP) ................... 2018-086653

(51) Int. Cl.
*C12Q 1/68* (2018.01)
*C12Q 1/6895* (2018.01)
*C12Q 1/6844* (2018.01)

(52) U.S. Cl.
CPC ......... *C12Q 1/6895* (2013.01); *C12Q 1/6844* (2013.01)

(58) Field of Classification Search
None
See application file for complete search history.

(56) References Cited

PUBLICATIONS

Yamamoto et al. Rapid detection of *Candida auris* based on loop-mediated isothermal amplification (LAMP). J. Clin. Microbiol., 2018, pp. 1-22.*
International Search Report dated Jul. 30, 2019 in International (PCT) Patent Application No. PCT/JP2019/017606.

* cited by examiner

*Primary Examiner* — Suryaprabha Chunduru
(74) *Attorney, Agent, or Firm* — Wenderoth, Lind & Ponack, L.L.P.

(57) ABSTRACT

A method for detecting *Candida auris*, including subjecting a nucleic acid sample obtained from a specimen to a nucleic acid amplification reaction by the LAMP method and detecting an amplification product, wherein, in the primer set to be used in the LAMP method, FIP is a polynucleotide including 5 to 20 nucleotides located on the 5'-terminal side and 5 to 20 nucleotides located on the 3'-terminal side in the nucleotide sequence represented by SEQ ID NO: 1, BIP is a polynucleotide including 5 to 20 nucleotides located on the 5'-terminal side and 5 to 20 nucleotides located on the 3'-terminal side in the nucleotide sequence represented by SEQ ID NO: 2, F3 is a polynucleotide including SEQ ID NO: 3, and B3 is a polynucleotide including SEQ ID NO: 4.

6 Claims, 3 Drawing Sheets
Specification includes a Sequence Listing.

US 11,753,689 B2

PRIMER SET FOR USE IN DETECTION OF *CANDIDA AURIS*, *CANDIDA AURIS* DETECTION KIT, AND *CANDIDA AURIS* DETECTION METHOD

TECHNICAL FIELD

The present invention relates to a primer set for use in the detection of *Candida auris*, a *Candida auris* detection kit, and a *Candida auris* detection method.

BACKGROUND ART

*Candida auris* is a pathogenic species of yeast which was first discovered in Tokyo in 2005 and was reported by the first present inventor as a new species (Non-Patent Literature 1).

Until August 2017, *Candida auris* discovered in Japan was found in a culture of a topically infected site (external ear canal) and has relatively low pathogenicity. *Candida auris* was just a single strain that was not drug-resistant, although *Candida auris* exerted slightly low resistivity to some of anti-fungal drugs (e.g., fluconazole).

After that time, however, virulence-increased multidrug-resistant strains of *Candida auris* which can cause sepsis and the like have been reported with the spreading of *Candida auris* all over the world including South Korea, India, North Africa, Venezuela, the United Kingdom and the United States. By 2016, *Candida auris* has been recognized as a world's first fungus that can cause global outbreak (pandemic) (Non-Patent Literature 2). In the latest report published in May 17, 2017, it was reported that 122 persons (7 persons in the last year) were infected with *Candida auris* in the United States and *Candida auris* had high mortality. In the United Kingdom, *Candida auris* has also been spreading, the number of infected persons already reaches around 200 persons, *Candida auris* is reported as "Japanese Fungus" by the media, and alert has been issued to medical/healthcare institutions.

Under the current circumstances, the infection by *Candida auris* is limited to compromised persons, and the outbreak of the infection occurs in the form of hospital-associated infection. From the view of the overseas spreading situations, it is considered that there is a high possibility that the hospital-associated infection is spread through nasal cavities, external ear canals and so on with a normal persons acting as a vector, as in the first case reported firstly by the first present inventor. Actually in the United States which has already been under the spread of the infection by the fungus, it is believed that the infection by the fungus is spread easily thorough skin such as fingers of a healthcare professional (Non-Patent Literature 3). Accordingly, there is a high possibility that a fungus that has acquired increased virulence and drug-resistivity overseas is imported into our country because of flourishing international exchanges and the opening of Tokyo Olympic Games, and it has been urgently demanded to prepare testing systems for preventing the import/export of toxic fungus before it occurs.

CITATION LIST

Non-Patent Literature

Non-Patent Literature 1: Satoh K, Makimura K, Hasumi Y, Nishiyama Y, Uchida K, Yamaguchi H. 2009. *Candida auris* sp. nov., a novel ascomycetous yeast isolated from the external ear canal of an inpatient in a Japanese hospital. Microbiol Immunol 53:41-44.

Non-Patent Literature 2: Website of the US Centers for Disease Control and Prevention (CDC), Tracking *Candida* auris (connected on Apr. 22, 2018).

Non-Patent Literature 3: Shawn R. Lockhart, Elizabeth L. Berkow, Nancy Chow, Rory M. Welsh, *Candida auris* for the Clinical Microbiology Laboratory: Not Your Grandfather's *Candida* Species, Clinical Microbiology Newsletter, Volume 39, Issue 13,2017, Pages 99-103, ISSN 0196-4399.

Non-Patent Literature 4: Nakayama T, Yamazaki T, Yo A, Tone K, Mahdi Alshahni M, Fujisaki R, Makimura K. 2017. Detection of fungi from an indoor environment using loop-mediated isothermal amplification (LAMP) method. Biocontrol Sci 22:97-104.

Non-Patent Literature 5: Shigekazu Iguchi, Ryo Mizushima, Keisuke Kamada, Yasutomo Itakura, Atsushi Yoshida, Yutaka Uzawa, *Yuko* Arai, Miyako Takaoka, SumieSato, Aeko Goto, Toshiko Karasawa, Naoki Tsuruoka, Daisuke Totsuka, Erika Ono, Manabu Nonaka, Koichi Makimura, Ken Kikuchi: The Second *Candida auris* Isolate from Aural Discharge in Japan. Jpn J Infect Dis. 2018 Mar. 22; 71(2): 174-175. doi: 10.7883/yoken.JJID.2017.466. Epub 2018 Feb. 28.

SUMMARY OF INVENTION

Technical Problem

However, *Candida auris* is a new species of pathogenic fungus (yeast), and cannot be discriminated from closely related species thereof (e.g., *Candida haemulonii, Rhodotorula glutinis*) by an automated identification system that has been commonly used in a clinical laboratory, such as VITEK2 YST card (bioMerieux, Maracy I'Etoile, France) and API20C AUX (bioMerieux). Accordingly, the type of the species of the fungi cannot be determined accurately. For these reasons, the establishment of a method for detecting (identifying) *Candida auris* with high sensitivity and in a specific manner is a major problem in diagnosis, treatment, clinical tests, control of hospital-associated infections, and epidemiologic analysis. Moreover, in order to make a treatment for *Candida auris* infection effective and prevent the spread of the infection, rapid detection ability as well as high detection accuracy are absolutely necessary.

The present invention has been made under these circumstances, and an object of the present invention is to provide a detection method which can detect *Candida auris* rapidly and accurately. Another object of the present invention is to provide a primer set and a detection kit which can be used in the detection method.

Solution to Problem

In order to solve the problem, the primer set for use in the detection of *Candida auris* according to the present invention is a primer set for use in the detection of *Candida auris*, which includes four types of primers consisting of FIP, BIP, F3 and B3, and is intended to be used in the detection of *Candida auris* by amplifying a *Candida auris* target sequence in a specimen by the LAMP method, the primer set being characterized in that:

FIP is a polynucleotide including 5 to 20 nucleotides located on the 5'-terminal side and 5 to 20 nucleotides located on the 3'-terminal side in the nucleotide sequence represented by SEQ ID NO: 1;

BIP is a polynucleotide including 5 to 20 nucleotides located on the 5'-terminal side and 5 to 20 nucleotides located on the 3'-terminal side in the nucleotide sequence represented by SEQ ID NO: 2;

F3 is a polynucleotide including SEQ ID NO: 3; and

B3 is a polynucleotide including SEQ ID NO: 4.

In the primer set for use in the detection of *Candida auris*, it is preferred that FIP is a polynucleotide including SEQ ID NO: 1 and BIP is a polynucleotide including SEQ ID NO: 2.

In the primer set for use in the detection of *Candida auris*, it is more preferred that polynucleotides respectively including SEQ ID Nos: 5 and 6 are further included as loop primers.

The *Candida auris* detection kit according to the present invention includes the primer set for use in the detection of *Candida auris*.

The method for detecting *Candida auris* according to the present invention is a method for detecting *Candida auris* including subjecting a nucleic acid sample obtained from a specimen to a nucleic acid amplification reaction by the LAMP method and detecting an amplification product, the method being characterized in that:

a primer set to be used in the LAMP method includes four types of primers consisting of FIP, BIP, F3 and B3;

FIP is a polynucleotide including 5 to 20 nucleotides located on the 5'-terminal side and 5 to 20 nucleotides located on the 3'-terminal side in the nucleotide sequence represented by SEQ ID NO: 1;

BIP is a polynucleotide including 5 to 20 nucleotides located on the 5'-terminal side and 5 to 20 nucleotides located on the 3'-terminal side in, the nucleotide sequence represented by SEQ ID NO: 2;

F3 is a polynucleotide including SEQ ID NO: 3; and

B3 is a polynucleotide including SEQ ID NO: 4.

In the method for detecting *Candida auris*, it is preferred that FIP is a polynucleotide including SEQ ID NO: 1 and BIP is a polynucleotide including SEQ ID NO: 2.

In the method for detecting *Candida auris*, it is more preferred that the primer set further includes polynucleotides respectively including SEQ ID Nos: 5 and 6 as loop primers.

Advantageous Effects of Invention

According to the method for detecting *Candida auris* of the present invention, it is possible to detect *Candida auris* rapidly and accurately. The primers and the detection kit can be used in the method for detecting *Candida auris* of the present invention.

DESCRIPTION OF EMBODIMENTS

Figure 1:
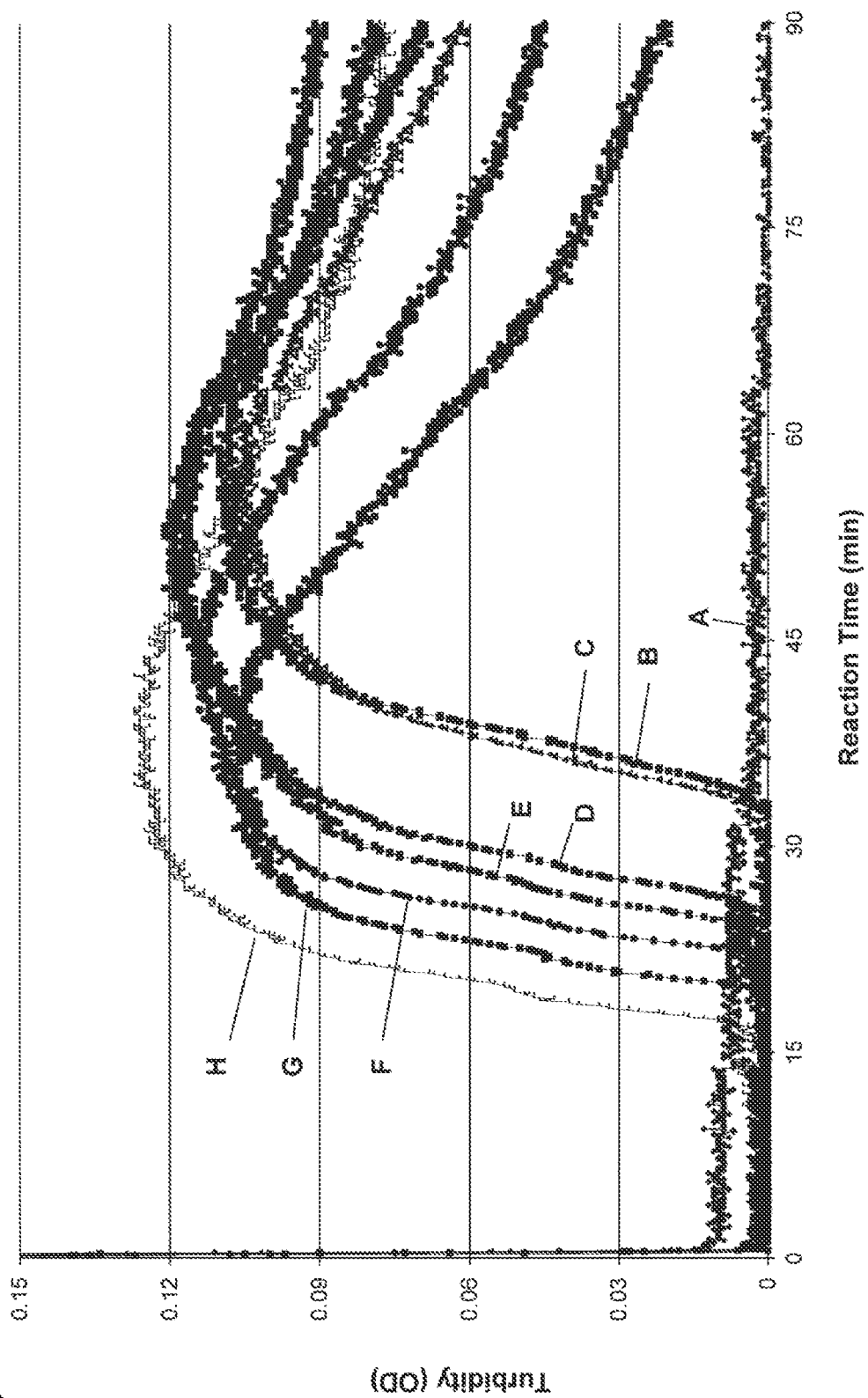
FIG. 1 is a diagram showing the results of the detection of amplification products by the detection method of the present invention using the LAMP Auris primer set using pTAC-2 Auris plasmid carrying a DNA fragment specific to *Candida auris*, in which the results are expressed in terms of the number of copies per detection reaction (copies/reaction). A: negative control (no reaction), B: $2\times10^0$ copies/reaction (34 min), C: $2\times10^1$ copies/reaction (33 min), D: $2\times10^2$ copies/reaction (26 min), E: $2\times10^3$ copies/reaction (24 min), F: $2\times10^4$ copies/reaction (24 min), G: $2\times10^6$ copies/reaction (22 min), H: $2\times10^8$ copies/reaction (17 min).

The present inventors have focused attention on the LAMP method as a means for detecting *Candida auris* rapidly and specifically and with high sensitivity. The present inventors have succeeded in the designing of four types of primers for amplifying target DNA of *Candida auris* specifically by the LAMP method and two types of loop primers for accelerating gene amplification. As a result, the present invention has been accomplished.

The LAMP method is known conventionally, and is a method in which amplification is performed by utilizing a strand displacement reaction using four types of primers which are combinations of six regions selected in the sequence for a target gene.

The designing of the primers in the LAMP method is carried out by utilizing six regions, i.e., F3 region, F2 region, F1 region, B1 region, B2 region and B3 region as observed from the 5'-side, in a region to be amplified (wherein the region is also referred to as "template (nucleotide, DNA)", hereinafter). Regions respectively complementary to these six regions are referred to as "F3c region", "F2c region", "F1c region", "B1c region", "B2c region" and "B3c region". In the LAMP method, four types of primers (two types of Inner primers (FIP and BIP), and two types of Outer primers (F3 primer and B3 primer)) are used. The Inner primers are respectively formed by linking F1c region (i.e., a region complementary to F1 region) to F2 region and linking B1c (i.e., a region complementary to B1 region) to B2 region. In general, the LAMP method has such characteristics that a denaturation reaction from a single strand to a double strand is not needed and the reaction can proceed at a constant temperature ranging from 60 to 65° C. when compared with PCR method, and also has such characteristics that an apparatus such as a thermal cycler is not required, the amplification speed is rapid, and the specificity is also high.

The LAMP method using loop primers is also known conventionally. In general, each of the loop primers is designed as a primer having a sequence complementary to a single strand region (a region between B1 region and B2 region, or a region between F1 region and F2 region) of a 5'-terminal-side loop of a dumb-bell structure in an amplification product of the LAMP method. The loop primers are called as "loop primers B(LB)" and "loop primers F(LF)", respectively. When the loop primers are used, the number of origins of DNA synthesis can be increased and therefore gene amplification can be accelerated.

In the method for detecting *Candida auris* of the present invention, as a specimen to be detected, a material such as a clinical specimen collected from a subject (e.g., blood, a tissue, ascitic fluid, a bronchoalveolar lavage fluid, and a skin, mucosal or external ear canal swab) or cultured cells can be used. These specimens may be subjected to the concentration or separation of cells, the isolation or concentration of a nucleic acid from cells, or the like as a pretreatment for an amplification reaction by the LAMP method.

A sample nucleic acid can be prepared in accordance with a known method from a specimen to be detected. As the method for preparing the sample nucleic acid, a conventional method can be employed, and examples of the method include a chemical lysis (e.g., Proteinase K) treatment, a physical disruption (e.g., bead disruption) treatment, an alkaline lysis method, and a method of purifying a nucleic acid by the extraction with phenol/chloroform or using magnetic beads, a silica membrane or the like (Non-Patent Literature 4). Alternatively, a commercially available nucleic acid extraction kit (e.g., Kaneka Easy DNA Extraction kit version 2 manufactured by Kaneka Corporation) may be used as required.

The primer set to be used in the detection method of the present invention (i.e., the primer set for use in the detection of *Candida auris*) includes four types of primers (FIP, BIP, F3, B3), and may also include loop primers (Loop-B, Loop-F) as required.

The primers (FIP, BIP, F3, B3) and the loop primers (Loop-B, Loop-F) include sequences respectively including the polynucleotides shown below. The primers (FIP, BIP, F3, B3) and the loop primers (Loop-B, Loop-F) are designed from the findings of the present inventors on the basis of a nucleotide sequence (target sequence) specific to *Candida auris* and suitable for the LAMP method.

A preferred embodiment of the primer sets of the present invention is shown below.

```
(Primer set for use in the detection of Candida
auris)
FIP:
                                       (SEQ ID NO: 1)
AGGCTACTGAGCTTGCTGGTGTAACCAAACCAACAGGAGAGG BIP:
                                       (SEQ ID NO: 2)
ACGGTTTCAGGGTTAGCATGGCTCAACAAAGTCGCTGGTACA

F3:
                                       (SEQ ID NO: 3)
GGGAAAGGAACCCTGACCT

B3:
                                       (SEQ ID NO: 4)
GGACACAGCATTCGAAGTGT

Loop-F:
                                       (SEQ ID NO: 5)
CATCTCGAAGGCCTCGGT Loop-B:
                                       (SEQ ID NO: 6)
CACATACTCGAACGGAGTC
```

The primer set of the present invention may include those a primer in which a design change, such as the substitution or deletion of a nucleotide in the sequence or the change in the length of the sequence, is made as long as the specific detection of *Candida auris* by the LAMP method cannot be inhibited. Particularly with respect to the sequence for each of FIP primer and BIP primer, about 10 nucleotides located at the center part of the primer may be an arbitrary sequence, or an arbitrary sequence composed of about 1 nucleotide to 200 nucleotides may be inserted at the center part. With respect to Loop-F primer and LoopB primer, any primers can act as the Loop-F primer and the Loop-B primer, as long as each of the primers includes a sequence that is complementary to a single-strand domain (located between B1 region and B2 region or between F1 region and F2 region) in a 5'-terminal-side loop of a dumb-bell structure of an amplification product of the LAMP method and is specific to the domain. Therefore, the sequences for the Loop-F primer and the Loop-B primer are not limited to the sequences represented by SEQ ID NO: 5 and SEQ ID NO: 6.

Namely, in the primer set of the present invention, FIP is required to be a polynucleotide which includes 5 to 20 nucleotides located on the 5'-terminal side and 5 to 20 nucleotides located on the 3'-terminal side in the nucleotide sequence represented by SEQ ID NO: 1, and BIP is required to be a polynucleotide which includes 5 to 20 nucleotides located on the 5'-terminal side and 5 to 20 nucleotides located on the 3'-terminal side in the nucleotide sequence represented by SEQ ID NO: 2.

In the detection method of the present invention, the nucleic acid sample in the specimen is subjected to a nucleic acid amplification reaction by the LAMP method using the primers (FIP, BIP, F3, B3) and optionally using the loop primers (Loop-B, Loop-F), and an amplification product is then detected.

The conditions for the amplification of the target sequence in the nucleic acid sample by the LAMP method are not particularly limited, and may be adjusted appropriately. A specific example of the temperature to be employed for the nucleic acid amplification reaction by the LAMP method is a temperature falling within the range from about 50° C. to about 65° C., and a specific example of the reaction time to be employed is a time period falling within the range from 20 minutes to 60 minutes.

In addition to the above-mentioned primer set, the *Candida auris* detection kit to be used for the detection method of the present invention can also include a polymerase, a buffer, dNTPs, $MgSO_4$ and the like as reagents for use in the amplification of the sample nucleic acid. The concentrations of the reagents to be used in the detection method of the present invention and the like can be adjusted appropriately depending on the volumes of the reagents, the reaction time and the like. As the polymerase to be used in the amplification of the sample nucleic acid, a known polymerase can be used appropriately. For example, Bst DNA Polymerase (manufactured by Eiken Chemical Co., Ltd.), Csa DNA Polymerase (manufactured by Nippon Gene Co., Ltd.) and the like can be used.

In the detection kit, the primer set and other regents may be included separately, or some of them may be prepared in the form of a mixture. The primer set consists of four types of primers and loop primers, and these primers may be included separately or some of them may be prepared in the form of a mixture.

Furthermore, in the detection method of the present invention, a known method may be employed appropriately for the detection of an amplification product by the LAMP method. For example, for the detection of the amplification product, a method in which the occurrence of white turbidity of a reaction is observed with naked eyes, a method in which the white turbidity of a reaction solution is measured using a spectrophotometer, and a method in which a fluorescence is detected visually, a method in which a labeled oligonucleotide or a fluorescent intercalator capable of recognizing an amplified nucleotide sequence specifically is used can be exemplified. Alternatively, it is also possible that a reaction solution obtained after the completion of the reaction is subjected to agarose gel electrophoresis without any modification, then the gel is stained with ethidium bromide and then a ladder-like electrophoresis image specific to an amplification product is confirmed by the irradiation with ultraviolet ray.

In the detection method of the present invention, the detection of an amplification product obtained by the LAMP method may include the detection of the presence or absence of the amplification product as well as the measurement of the quantity of the amplification product.

In the detection method of the present invention, the nucleic acid sample in the specimen is subjected to a nucleic acid amplification reaction by the LAMP method using the detection kit including the primer set, and an amplification product is then detected. The primer set is designed employing a nucleotide sequence specific to *Candida auris* as a target.

In the detection method of the present invention, *Candida auris* can be detected specifically with high sensitivity without detecting a closely related species thereof. Therefore, *Candida auris* can be detected accurately even when a specimen contaminated with various microorganisms (e.g., a contaminated clinical specimen, an environmental specimen) is used. Furthermore, in the detection method of the present invention, the time required for the detection is short (about 20 minutes to 60 minutes) and therefore the detection can be achieved rapidly.

The *Candida auris* detection method, the primer set and the detection kit of the present invention are not limited to the above-mentioned embodiments.

EXAMPLES

Hereinbelow, the present invention will be described specifically by way of examples. However, the present invention is not limited in any way by these examples.

<Example 1> Designing of LAMP Auris Primer Set

In order to design a primer set to be used in the LAMP method, the genome sequences for four types of *Candida* species, i.e., *C. auris* (PRJNA342691), *C. tropicalis* (GCF_000006335.2), *C. albicans* (GCA_000182965.3) and *C. lusitaniae* (LYUB00000000.2), were aligned and were compared with one another using Mauve (version 20150226), and a sequence having low homology with other *Candida* species was searched for. As a result, about several hundreds nucleotide sequences were obtained.

Most of the several hundreds nucleotide sequences were not suitable for the designing of primers. On the basis of the technical knowledge based on the experience of the present inventors, four types of nucleotide sequences (candidate sequences) that were assumed to be used for the designing of the LAMP primer set were selected (SEQ ID NOs: 7 to 10).

(SEQ ID NO: 7)
CACTACAGCAGGATCAACGGATGCTTCATACTCTGAAATCACCTTTAATG

CTGGGATTGGCGCCCACACAAAGTTGGCTGGGTGGACAAACTCCTCCACA

GAAACAGAACCGAAACGGCCAGCGAGGAACAACGAAGCAGCAACGTCAGC

CTTCAAGGTTGAGCCAGCATCCGAAGATACCACAACAACCTTGCGTGCAG

ACGAAGGCACAGAAGCCACGAAGTGTTCTTGAGCAAATGGGAAAGGAACC

CTGACCTTAACCAAACCAACAGGAGAGGAAACCGAGGCCTTGGAGATGAC

ACCAGCAAGCTCAGTAGCCTGGTGAGCACCAAAAGCGACAAAAACAGTTT

CAGGGTTAGCATGGCCCACATACTCGAACGGAGTCAAATTTGTACCAGCG

ACTTTGTTGAACACTTCGAATGCTGTGTCCACTGCCTTTTCCAAAGAATA

GTCGCCGTCGGGAATCGAAGACACCAATTGCTGGTATAAGCGGCCCACAT

CGGTCACAGACAAGATGTCATCGAACTTGGAGATCGCTTTAGCAAACTCA

GGACCGTCGAAAACGTGCAAGGCTGGTCCCTGAAGCAAAGTAGCCACAAA

GTGAGTGAAGATGGTGATGTACTGCAACTCCACGGCGCTCTGCGAGTCCG

CCGGGGCCACCACAGGGATACCCGTGGAGCGAGCAGTTGCCAAAGGAGTC

GTATAGTTTGAAACCAACGAGTTTGTTTCCACATCAAAGTCGATAGCGGA

AACGTTCAAGGTCAATGGCAATTTTGCAGCCTTGGCCAAAGTGGGCTGCA

TCCATGGCAAGGCGTTGGCGCCCAACACAGCAGTATGTGGTCCAGTGGAG

GACACGTTGCTAGCGGCATAGC (SEQ ID NO: 8)
AGTAAGAGCTGCGGTCATCAAGCTCAACATCTTCATCGTCTATCGCCGAC

AGAGACGCCTCCATTTGGTTTTTTCTTGTTAAATTGTCCACCGACAAAGG

CTGGTGGCCTGAAGTCTCCGCAGAGTCTGCCATAAAGTTTGAGCAATTGT

AGATGTTGTAGGTTTTTTTTGCAAGTGTTATCGGCGTCCGAAGTTGAAGT

GTGACGGGCGCGCAGGAAGGTCAGAAAGCAGCAAGGAAACGGCCAAAGGT

ACCAGATAGAAGAAACGGTCTGTTGGGGCTGATTTTGTAGAAACTGATGT

TTAATTCACATTTTCTTCACCCGTGGGGTTCGTTGGGAACCGTCACGAG

GCACGTTTGTTGTGGGGCACGTGTGGTTGCAAAATGAGATAAGCAAGGTA

GTGTGGTTTGACAGCTTCATATAGGAAGGTGCAAAAAAGTGCAAAGAGAG

AAGAATGTAAATTGAAATTGTAATATTCCAATGAGTGAAGTGCTAATTTT

GGAAATCTGAGCTTTTTAATGTCTACTCAACTTTGATGTTTCAGTGGATG

AAGCCTGTTTGGCGTAAAGTCCACAGGTTTTCGGAGTTTTGGCGAGCATC

GACACATAACAAGGCAACAATGCAAAGTCACGAAAATCTCGAACAATGGC

GAGTCGTAAATTGGGTCTCTGATTTTCCTAGCGTGAATTGAACAGAAACA

GTCCAAGTCCATGCTTGCATTCAGTCACTTGTTTTGAGATGTGGCCGGTG

AGAGCCACTGAAAGCGAACCACATACATGTATCCATAATGTACACAATAA

AGGCTCCTAGATCAAAGGATCAAGCTCATAATACAAGCAACAACGCCATC

GTGTCAGCCGAGCTATTTGAGTGTCACCTGAAGAATAATACCCATACTTG

CGCTCTTAAGTGGTAGTATCTGCTGAGCGTCTATCTGATCTGTTGAACTG

CTACCACGAGCTTTGGGGATTTTTCGCAGCAATTATACCTGGGCAAATAC

AAAGCACAATATTCACAAGCACAGCACTTGTAGGCGACCTCATGCCACTG

GTCTGATTAACAAACAATAAGCTTTTGTTTGATAAAACTAATAACGGATC

TTGCGAGGGTGATGTAGCTATGAAGAACATGCATGCAACCTCAGCCAGCA

TGAGGTATTAGCTCGTAGAATGGCTACGAAGAGACCTAAACAAAAGTAGA

AGTAAGTTTAAAGCCTTTCCGATGGAATTTAACAAACTACAAAGTGGAGC

AATTCTTTTTGTCGGCTGTTATCTGCTTGAGTGGTATTCATCACGCTGTC

TGTGCTCCCGAGGACTCTCCGATACCACAAACTATAATGTTAAATCCACA

TATTTTACATGAGCCGAGATGAAGTTATGCAGACTCAACACAAAGGAAAT

CAGGGGTCGTATCTTAAGTTCTTCTTGTTTCTAATAATCCTCTCCAGAGG

ACTCCATTTGCAGCCACAAATACCTCATCGCGAAAAAGTGCAGCTTCATC

TCACTCCATAACTATGTCAGCTGCCGTCGAAAC (SEQ ID NO: 9)
ATACTTCAACGAAGGAGATTACTTCCAATTTCGAAGCAAAAGATTGGGGT

CAGAAGAGCCCAAGTCACCAAGGTCAGGTTATGACTCGACAAAGCAAGCA

ACAGCCGACGAAGATAAATCGGAGGGAGATGAGGACGATATATTAAATGA

GGGAAACCTCCATTTCCTTGACTTTATTGAGAATAAAACCTTTGGTGTCA

```
ACCCCAGATCAAAGTCGGTCTTCGACCGCCTGGCATACGACTCTGTTGCT
TTCATGTCGAACGATGCTGAGGAAGAGGAAAAGGAGAAATCTCTCACGAC
TACCTTAGAAGTTCTTGTTGCTCCAGATTCTCCGCCTCCAAGCGATTACG
TGATCGATCTTATTCACGAGATATCATCAATTTGCACGGACGTAAAACTC
ATGTTACGTTCGCTCAATGTGAAACAAATGTCGAAAGCGTTGAAGCAGAC
TGAGGAGGACTACCACAAGCTTGAAAGTTTGGCTCGTCAAGAACGTGAAA
CCGACGAAGACAACAATCTGCAAATCACTATGAAACAGACGTCACCTACT
AGGCCATCGGTGACGACGCTAAAGACGGGCAGTGGATCTGTGGCTTCTGT
TCCGTTCAGGCGTCTGCAAACACTGGAAATCAGTGAGCAGATTCCGCCAC
CGTCGCAATTGCAAGGCATGAGATCGTCAACATCGCTCAACACCACAACA
TCGGCTCTCAAATTCACGCCTCTTAAGTCTGCAACAACAGGTGGTAAAAC
ATTTTCTAAGGGCCTGCTCGAAGACAACAAAGATTTGGACCGGCGCATTG
CACAACTTGTGAAAGAAGATGAGAAGAAGAAGCTGAAGGCTGCCAAAGAA
GAGAAGCAAAGATTGGCGAAAGAAGAGAAGCTAGCTGCTAAACAAAGCAA
GCAGAGGGAAAAGGAAAAACAAAGAGAGGAGTTGTCGCATACGAAGCACA
AGGCTACTCCTCTTGAAAGGAACCATACTGAGCCACAAGACTTCTTCTCT
ACGAAGCTGAACCGCGAAGATACCGATGAGTCTTCGTTGTTTTCGAAGCC
ATCGATCACTTCGAAAGACAAGAAAGGAAGCATTATACTGCGGATCGGAC
ACAAACTCAAACATACCGAGCCGCTCAAGCACACGGAGTCTGTTGACAGT
GATGTGAGGAGTATTTCCACAACTAAATCGTCCAGTAGCCAAACGTCAAA
CACTAGCAAGAAGTCGTCACGCAAGGTTGGATTATTTGGGTTGCGCAAGA
GGAATTGAGAAACAAAAGGCAAGAGAGAAAAAAAAAAAAAAAAATATATAT
ATATATACTAAGTTGGAGGAGAAATCAATCTGCTCCTTGTCAGTGTCTTT
TGGAATGATTGCATCGTAATATTCTTTTCTGGAGATTTTTTTGGGTTTT
TTGGAACAGCTGCAACACCATCAACACTCTGAGAAACAACTCCCCGAGAC
GCGCCAGCTGCGGCTGCCGCGTAGGAAAGTTGAGCCCCACTGGACTTTTG
AGAAGTCTGGGTGCCGGAGGAGGGACCTTCGGCGCGATTTGGGGAGGAAG
CAACCTTAGTTGCTTTCTCCAGGATCATTGGATCGCTGAGCAGGGAGTTT
CTGTTCTCCTGACGCGTACCGCCTTCTACGGATGCGACGCTAGAAGATAC
AGAAACACCTTTTCCAGGACGATCAAACTCGATAGGTGGTTCAGGAGGTC
GGGAATCTCGCTCCACGGTACCGGAGGTCGATTCGCGCCTTCTGCTTGA
TGCCGAACGATATTATTCAGCATTTTTCAAAAAGGATCTAAGGGTGTAAG
CTTGAGCTTGTAAATGTATTCTAGAACACCGAAGTATTTAAAACTTTGCT
TTGAGTCTTTTATTGTATTATTAACTACTGTTTACTATTGCTGTCATATT
GAACACCTTTTTGAAATTCGCCAC
                                        (SEQ ID NO: 10)
CTTCGTTGCGTTGAGAAGCGCCTTGTCCAACTTTTTGGACTGCTCTAAAA
AGCTGCGAAGCTTCTTAGACTTGGAGTAAACTTGTAGGAATGACACGGCT
ACACCTTGAAGAAGGGTGATGGGGGGAGTGACTCCTCCGTGAACGTAGAG
CATGTACATGAAAGTTGCGTAGAGGCCACCTTTCGAGCCGGCAACAAAGA
TCTCAAATACTTGTGTGTAAATGGCTTGTTCTCCCACACACGTTCTGAA
```

```
ACATCTTCGTCGTCGGGATCCTCGTCCTCATCGCTGATTTCCTCATCATT
CGATACCTCGTTGCCACCCGGCGACAGCAATCCCTGATTATTGGGGATGG
TGTAGAACATGAGCTCATAAACGTTGAGTACGAGTTTACCGAAGTATGCT
ATTGCTTCCATCCCGAGCACTCCGTAGTGGATACCAAACAAGAGACTACC
AACAGAACGTGTGCCCTGGAAGACGTCGTAAGCCAAAAACTTCGCTAGGA
GGAGGTCGGCGACAGTAAATACCTCGAGAAGAATCAGAACCCTATACGTG
GCGAAGTTGTAGAAGACCTGGCGAGAGGTTGATATCTGATGCGGAATCAT
GTTCGTGATTTTCATCTGAAACGAGTCAAGACGGTCCGTCATGATGATAT
GAAACACTTTGAACATGATCGTGAGGTTGATCCACACTATATTGAGAAGA
AGATTATCGTCACTAAACATGATTATGAGAAGATTAATAAGGTAGAAGGG
TAACTCCTCCGAAATATGCTCAATTTCAATGATCCGAAGCTCTCTGAAGA
TCAATTTGATCCCTGCAAACCCCATGAGAATAAAGCAACTTACCACGAAG
TTGAGGAGAATTAGGAGTCTCACGCTCTCCGTGAGCTCGTACATCATGGT
AAGATAATCGACAGAGTTCATGGCCAGAACCACGAGCGATGCAGCGAAAA
GGCCGAAGCTAATGCCGCCATACACTGCAATTGCAATGGTGCCCTTTCGA
GGCATGGTTATGGTGTTTTGTCTTTCTTTTGTGGGGACGAAAGGTGTGGA
AGCCGGAAGTAAACACCTCACCTTCGCGATAATCCTAGATCTACGCTAAC
TTGCGCATAGAGGGTCGTGCGCGCAAAATTTTCCCCAGACTTCCAATTAG
TGGTCGCTTGAGTCTATTAAAGTTGCGGAATTCGGGACTTATGGAGGTCA
TTGCGTAATGGTGACATTTCAGTTCGTCTTCTTTTGATGTCTGGAATCAT
GCTCTGTCCGTTTAATTGCCTCATAGGCAGCCTCAGTGGCAGTCTCATGG
GCAGTCGCAGAGGTGATCTGGATGCTGGTGAAGTTGCCGGGCGCTTCAAT
TGAGCAGGTGATCTTTGTAGCTCTGACAATGATTGGGAAAATATTTTGAG
GTTCTTCTCGGTGTGATTTAAGTCGCGAGAAATTCCGTGGTAGTTCTTAT
CGATCATGTCGGATACAATATGTGCCTTTTGAGTTGCAGCTTTCTCTATA
GAGTCCGCCTGGCTGCGACTAGTATTGGTAATATCAGCCAAAGCATTATC
AATAACTTGTTTGGTCTCCTTCTGTAATCTTCCAAAGGCTCCCTGCACAT
CTTTTGGTGGCAACCTCTTTGAAGGACTTGAGATCCGTGGCCACTGACTTG
GTCTTTGTTGATATCGACTGTAGCGTTTGGGAATTTTGATGAATGTAGGC
CTGATACTCTTTGCTTAGAGTTGTCTTCTCTTCTTGCATGAATTCTGTTG
CACTTTCCCTAACCGCCTCGGCATTGCGTCCTTGCTTGACTTCACGAAC
CCGTCAAATGCTAGGTGCATTTGTTGCATATATTGCTCCTTAAGTGCCTC
ATACGTCTCTGCCATACGAGCCTTGAACTTCTTCTCAAAGGCCTTGTACA
TTGCGGAGTCTTCCAGAAGATGTGTTGAGTTGATGTAATCCGTTAGTTGC
TCATTCCTCTTGTTCACTCCAGCTACGTGCAGCGAGAAATCGAGGTTTTG
ACAAACATTATGAAGGGTAGAAAAGTCCATCAGATTAGCGAGAACCTGCT
CGAAGGCTGATGTCTCCTTCTCTACTTTGGAAGAAACATCATTTAATTTG
CCCTCGAGAGTCTTCTTAAAAAGGCAAAGATGCGTTTGAACGACGGTGGG
GATCTCCTTCACATTCAGCAGCACCTGAGTTAGGTCATTAAGATTGTTAA
TCACCTCATTAACGTCCCTAATGATACTCAGAATTCCAGTTCCTGTAACA
```

```
TTAGAGACTCGCTCTTTTTGAGAGCTGTATTTGTCTTTTAAATGCATGAA

CTCTTTTGTAGTCTTGTGAAGCTCAGCGTCTTTAGCTGCGAGGTCCAGCC

TGCTTTTCGAGTTCTCGCTAAGTGTTTGCTCGATCTGTAGTTTGAGTTCT

GCAATATCCTTGTCCCTCCCTTGAAGTTTGGCGTGTAGCCCTGTAATCTG

AGTGTCTTTCTCCTTCAACTCGGTTCTAAGTTCCGCAATTTTCCTTTCAA

AGTCCTCGTAGTTCTGAAGACTGATCCTGATGCTGTTGTCTTTGCCTTTT

GTAGCCAATAAGTCTCTATTCAATCTAGAAATCTCCGCTGATAACTCCCT

TATCTTTGTACGTTTGAGAACGAGCTCGCTGTCGGCCGTCGATTGTGGTA

TATTTTTGATATTCTTCGCCTTGGAAGCGTAAGTTAGCGTCAGCATCGTT

TCCATTAAGTTCAGCTTTGCCGGGGAAATGGTAGCAATCAATGCGGTTTT

GGTCCGCCCTCCAATAGAGCCTTGAAGAAGACGGGTGAGTTTAGACTCTC

TATAAGGTATATGTCTAGGTTCTTTGCCTTCACTCAATGCACTGATGACC

TTTCCCAAAGTCAAAAGACTCTGGTTGATCAGGCCCGCTTCTTTGGCACT

AGCATCGGTAGCGCCAGACTTGATGATATCTTCCAGCCCCGCGAGATCCA

CCAAATTCATTTTTGACAGCCGCACCACCTCTTGCCCTGACGACGACATT

ACTGTTTTGTGAAGCGTTATGGTGAAAATGGTGTGAGAACGTGATGAGCG

GGAGTTGAGTTTAGTGGTACCCATCTTCCTCTTCCCTAGGCACTTTTGTA

GCATCTCAAACCCCAGCTTCGCATCCACCACGTCAAGCTCATACAAATTC

TGGATCATTGTTCCCCTTCCATCTCTCGAACCATCCCCTAGGAGCCTTAG

TTTCGGCTTTTTGAGTTCAACTCAAGCTCATCGTTGACGAGATCATGGA

GCTCTTCCTTGTACAATTCCACACACGACAACTTGACACAGATGTCGTCT

TTGGCCACCTGAAAAAGCTCTTGCAACACACGAGGCACAATACCCGCATG

CTCTCCCACTAAATCCCCAACATTGTATACGTCTTTCCTGAGCCTGTCA

GGCCATACGCAAGGATAGTGACATTCATGCCTGCCATGAAATCTCGAAGT

AACGGACGAGCAATGTTTTTGTAAATGAGTTCCTGATCAGCATTGGCACC

ATAGACTTGGTCTAGTGTAAATACTTTGCCTGAACCGTCTGATCCAGAGC

CAAAGGAAGTGTTGGGGAAGCATTCACGCTAACGTAGGGTTCATCCGTG

GAACAGAAATCGTCAGGCACCGAGACCACAATCGGGGACTGGCGGCTAT

CTCCAGCTCAGTTCTTCTTCGCACACGGGCGCTGACCTGGATTTTGTCGG

ACATATAGTACAGTTTTTTTTTGTAGTCTTTCTTTGTGGAGATTATGGT

GATGTTTATGTTTGTTTACGATGGGCGGCCTGTGTGCAGGTCGGAACGGT

CAAAGCATGTAGAGTGTCTAGAGTCTTTATCGATGAATGGAAGTAGAGGA

GGTAAAATTCTAATAGTGAGATTCTTTTTTCGATGGACGTGTTTTTGTTT

ACGTTCCTCGTACTTAGTTATGTTTCGGGTTTAATGGTGTTTAGTGAGAA

ATGGCTGCAAAATGCAAATGCTGCGAAAAAGTATAGATCAGAGAAAGAC

AATACTACTGTCTGATAAAAAACAAAAGTTGATGATAAGAATACCAGAAT

TTGTACTCACATATAGGAAATCACCTAGAGTTTGATATATAATCTGACAC

AGCAATGTCAAAATCGCTTTTACCACGTGCTATAAAAAGTTTCTAAGGAC

GTCACCTTCTCGATATAAGATAAGCATTCTGTGAACGGCTGTTAGGAAAG

AGCATAGTGAGGTATTTCAGTTGAAATACGTATGCCAAAAAAAGGCAAC

CATTAATTAGATTCCACGTGGTTCACTACACTGAAAACAGATGAACTGTC

TACAATACAGTCTGTCAGTGCAATGCCTACCAGTTGCTGGTGGCATAGCA

CCTCACGAATGGATATATTCGCTACCAGGTTTTGTACAGCTCAAACCACT

ACATAGCTGGTTTCTGTCAACCTCGTCGCTATCAACTAACAAACTCTTTT

ACTAAAAAAGAGAAGCTCTTCTTTCACTACACGTACTGTACTAGCCTTCG

CTCGTGTGACGATTAGCCAGCCGTACTTTTCCCCATCACCGTAAACCATC

TATTGATGTTCATATATACAGATTCCAATGACGACGCCAATGGCAATGCC

ACGAGCCCCCAAAAACCTCAATCAAAGAAATCATCGTCATCTTCAT
```

Among from the sequences represented by SEQ ID NOs: 7 to 10, the nucleotide sequence represented by SEQ ID NO: 7 was selected as a sequence having a length of about 1 kbp and most suitable for a LAMP reaction on the basis of the experience of the present inventors. As the result of the BLAST search in the National Center of Biotechnology Information of the United States, it was confirmed that the nucleotide sequence represented by SEQ ID NO: 7 was the genome of *Candida auris* (*C. auris*) containing a pyruvate:ferredoxin oxidoreductase domain (accession number of the genome: XM_018317007).

The DNA fragment represented by SEQ ID NO: 7 was amplified with EcoRIdAmp (registered tradename) PCR Master Mix (manufactured by Takara Bio Inc.) using *C. auris* JCM15448 T that served as a template and a pair of primers consisting of Auris F (SEQ ID NO: 11: GCTATGCCGCTAGCAACG) and Auris R (SEQ ID NO: 12: CACTACAGCAGGATCAACGG).

In order to produce a pTAC-2Auris plasmid that was specific to the DNA of the fungus, an amplicon was purified with QAquick (registered tradename) PCR purification kit (Qiagen, Venlo, The Netherlands) and was then cloned into a pTAC-2 vector using DynaExpress TA PCR cloning kit (BioDynamics Laboratory Inc., Tokyo, Japan). The cloned nucleotide sequence was confirmed using ABI PRISM (registered tradename) 3130x1 Genetic Analyzer (Applied Biosystems, Foster City, Calif., USA).

A candidate LAMP primer set was designed using a 192-bp fragment (gene locus XM 018317007: located from 774b to 965b) as a target and using PrimerExplorer V5 software. The decided LAMP Auris primer set (also sometimes referred to as "LAMP Auris primer set", hereinafter) is shown in Table 1.

TABLE 1

| Primer | Sequence (5'→3') |
|---|---|
| FIP | AGGCTACTGAGCTTGCTGGTGTAACCAAACCAACAGGAGAGG (SEQ ID NO: 1) |
| BIP | ACGGTTTCAGGGTTAGCATGGCTCAACAAAGTCGCTGGTACA (SEQ ID NO: 2) |
| F3 | GGGAAAGGAACCCTGACCT (SEQ ID NO: 3) |
| B3 | GGACACAGCATTCGAAGTGT (SEQ ID NO: 4) |
| Loop-F | CATCTCGAAGGCCTCGGT (SEQ ID NO: 5) |
| Loop-B | CACATACTCGAACGGAGTC (SEQ ID NO: 6) |

It should be noted that the designing of the LAMP primers is not always easy even when a specialized software is used. For example, in addition to the basic LAMP primer set represented by SEQ ID Nos: 1 to 4 shown in Table 1, a primer set including the polynucleotides represented by SEQ ID NOs: 13 to 16 can be mentioned as another example of the basic LAMP primer set which can be designed on the basis of SEQ ID NO: 7. The primer set was confirmed to cause no *Candida auris* gene amplification reaction by the LAMP method.

```
                                              (SEQ ID NO: 13)
GTGGTATCTTCGGATGCTGGCTCCAGCGAGGAACAACGAA(FIP)

(SEQ ID NO: 14)
ACAACCTTGCGTGCAGACGAAGGGTTCCTTTCCCATTTGC(BIP)

(SEQ ID NO: 15)
AGAAACGGAACCGAAACGG(F3)

(SEQ ID NO: 16)
CCTCTCCTGTTGGTTTGGTT(B3)
```

<Example 2> Amplification Reaction by the LAMP Method

With respect to a cultured *Candida auris* specimen, an amplification reaction by the LAMP method was run using Loopamp Turbidimeter RT-160C (manufactured by Eiken Chemical Co., Ltd.) at 56° C. for 90 minutes. The reaction was terminated by deactivating the DNA polymerase at 80° C. for 5 minutes. Each of the reaction solutions was prepared by mixing 12.5 µL of 2× Reaction Mix (manufactured by Eiken Chemical Co., Ltd.), the primers of LAMP Auris primer set (40 µM of FIP, 40 µM of BIP, 20 µM of Loop-F, 20 µM of Loop-B, 5 µM of F3, 5 µM of B3), 1 µL of BstDNA polymerase, 2 µL of a sample DNA solution and distilled water together, and the total volume of the reaction solution was adjusted to 25 µL.

In order to determine the detection limit of the LAMP Auris primer set, pTAC-2Auris was serially diluted ($1 \times 10^0$ to $10^{10}$ copies/µL) and was used as a template in triplicate reactions. The detection of an amplification product was carried out with Loopamp Turbidimeter RT-160C.

The results are shown in FIG. 1.

As shown in FIG. 1, according to the LAMP method using LAMP Auris primer set, it was confirmed that pTAC-2Auris was detected and the sensitivity was high even when the concentration was $2 \times 10^1$ copies or less per one reaction. With respect to the extraction of DNA from the fungal cells, it was also confirmed that the DNA was extracted with high efficiency even when the fungal cells were treated with a DNA extraction reagent directly (i.e., without being disrupted).

<Example 3> Evaluation of Specificity of LAMP Auris Primer Set

In order to evaluate the specificity of the LAMP Auris primer set to *Candida auris* (*C. auris*), 57 strains in total of 38 species (20 kinds of filamentous fungi and 18 kinds of yeast strains) were tested (Table 2).

The full-length DNA of a template strain was extracted and purified in accordance with the method disclosed in Non-Patent Literature 4. With respect to the yeast strains, an aliquot of a colony proliferated on Sabouraud dextrose agar (SDA) was suspended in 25 µL of distilled water, and the resultant suspension was heated at 100° C. for 15 minutes and was then centrifuged for a short time. In each of the reactions using the LAMP Auris primer set, 2 µL of a supernatant or purified DNA was used as a template.

The results are shown in Table 2.

TABLE 2

| Species | Strain No. | LAMP Auris reaction result |
|---|---|---|
| *Acremonium curvulum* | NBRC32242 | − |
| *Aspergillus fumigatus* | TIMM0108 | − |
| *Aspergillus niger* | TIMM0115 | − |
| *Candida albicans* | LSEM11-828 | − |
| *Candida auris* | CBS12323, CBS12372, CBS12766, CBS12767, CBS12768, CBS12769, CBS12770, CBS12771, CBS12772, CBS12773, CBS12774, CBS12775, JCM12373, JCM15448$^T$, LSEM52-3435, LSEM52-3449 | + |
| *Candida duobushaemulonii* * | CBS7799 | − |
| *Candida famata* * | NBRC0083, NBRC0623 | − |
| *Candida glabrata* | CBS138, NBRC0005 | − |
| *Candida guilliermondii* | TIMM0257 | − |
| *Candida haemulonii* * | JCM3762 | − |
| *Candida krusei* | TIMM3378 | − |
| *Candida lusitaniae* * | NBRC1019, NBRC10059 | − |
| *Candida parapsilosis* | ATCC22019 | − |
| *Candida pseudohaemulonii* | JCM12453 | − |
| *Candida sake* * | NBRC0435 | − |
| *Candida tropicalis* | ATCC750, TIMM0313 | − |
| *Chaetomium globosum* | TSY-0369 | − |
| *Cladosporium carrionii* | TIMM3048 | − |
| *Cunninghamella bertholletiae* | TIMM3392 | − |
| *Exophiala ieanselmei* | TSY-0396 | − |
| *Fusarium oxysporum* | TSY-0351 | − |
| *Fusarium solani* | TSY-0403 | − |
| *Malassezia furfur* | CBS1878$^T$ | − |
| *Malassezia restricta* | CBS7877 | − |
| *Microsporum gypseum* | NBRC5948 | − |
| *Mucor circinelloides* | TIMM3177 | − |
| *Paecilomyces variotii* | NBRC4855 | − |
| *Pseudallescheria boydii* | TIMM0886 | − |
| *Rhodotorula glutinis* * | LSEM 20-1447 | − |
| *Rhodotorula minuta* | TIMM6222 | − |
| *Saccharomyces cervisiae* | LSEM14-1013 | − |
| *Scopulariopsis brevicaulis* | NBRC4843 | − |
| *Scopulariopsis brumptii* | NBRC6441 | − |
| *Scytalidium lignicola* | NBRC104988 | − |
| *Trichophyton benhamiae* | SM103 | − |
| *Trichophyton mentagrophytes* | TIMM2789 | − |
| *Trichophyton rubrum* | TIMM2659 | − |
| *Trichophyton tonsurans* | NBRC5928 | − |

+: positive,
−: negative,
* a species which *Candida auris* (*C. auris*) has been misidentified as in common tests.

By the LAMP method using the LAMP Auris primer set, the occurrence of amplification was confirmed with respect to all of 16 kinds of *C. auris* strains. In contrast, with respect to all of the remaining filamentous fungi and yeast strains including fungi which *C. auris* has been commonly misidentified as (i.e., fungi that have not been identified as *Candida auris* (*C. auris*) in the conventional test methods: marked with asterisks in Table 2), the occurrence of amplification was not confirmed.

In order to verify the quality of the DNA templates used in the reaction with the LAMP Auris primer set, the DNA templates were separately subjected to the LAMP reaction using panfungal LAMP primer set (Non-Patent Literature 4). As a result, the occurrence of amplification was detected with respect to the templates from all of the test species.

<Example 4> Detection of Candida auris (C. auris) in Clinical Specimen by LAMP Method The LAMP method using the LAMP Auris primer set was applied to a clinical specimen. The test was carried out on an ear swab specimen obtained from otitis induced by C. auris LC318417 (Non-Patent Literature 5).

An ear swab specimen was placed on the surface of SDA agar and was then cultured at 37° C. A small cream-like colony (cells) thus obtained was identified as Candida auris (C. auris) by the LAMP method of the present invention, MALDI-TOF MS (Bruker Daltonics K. K., Kanagawa, Japan) and rDNA sequencing.

At the same time, it was attempted to detect Candida auris (C. auris) DNA directly from a clinical specimen without carrying out culturing in the following manner. A cotton swab was placed in a 2-mL-microtube, was then washed with 1 mL of physiological saline supplemented with 0.05% Tween 80, and was then shaken for 10 minutes. A suspension thus obtained was centrifuged at 20,000 g for 10 minutes to produce pellets, the pellets were washed with 100 µL of physiological saline, and the full-length DNA was extracted using Kaneka Easy DNA Extraction kit version 2 (manufactured by Kaneka Corporation) in accordance with the instructions by the supplier. A nucleic acid amplification reaction by the LAMP method was carried out using the extracted DNA (2 µl) as a sample nucleic acid for an LAMP reaction solution and using the LAMP Auris primer set. The reaction conditions and the method for the detection of an amplification product were the same as those employed in Example 2.

Figure 2:
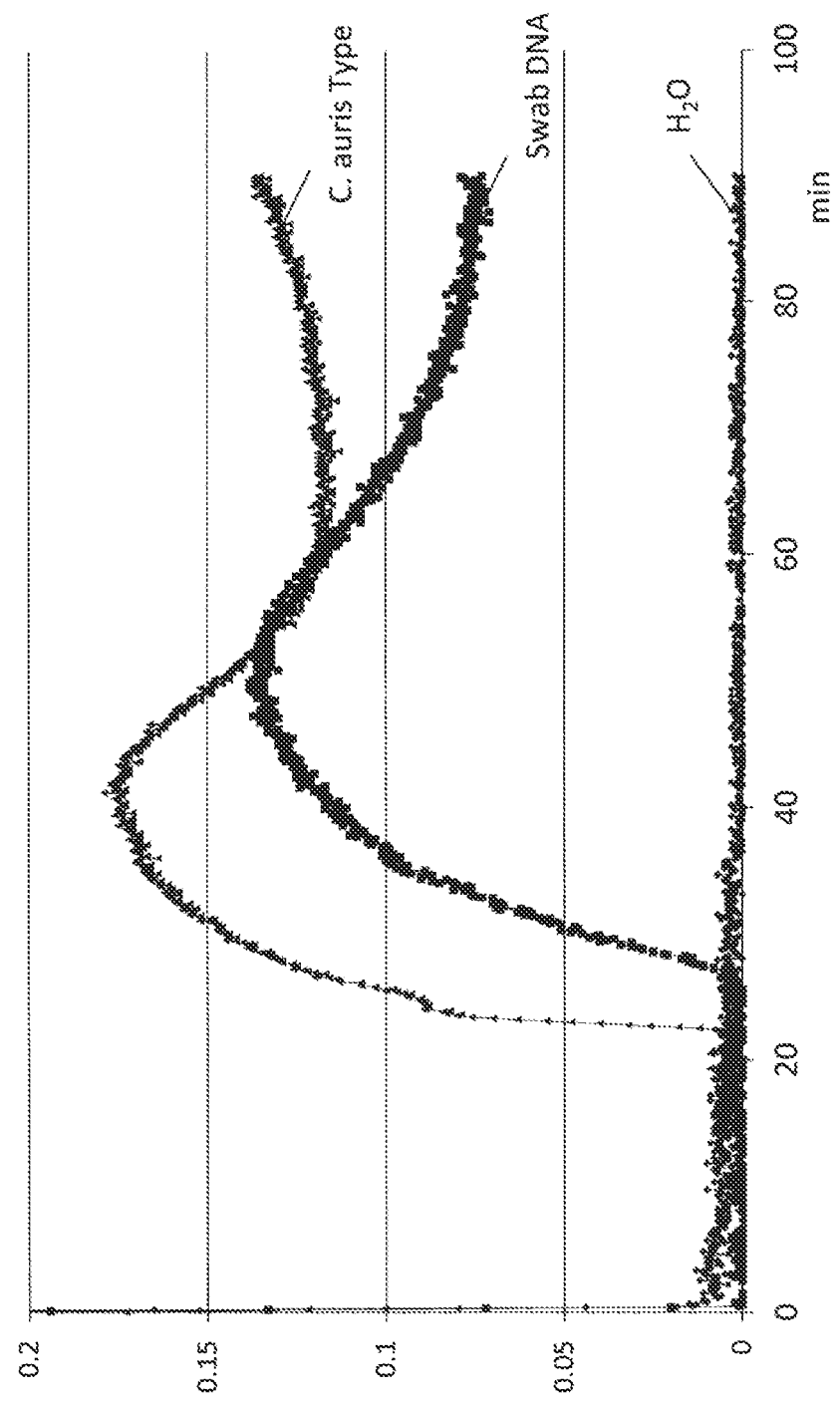
FIG. 2 is a diagram showing the results of the detection of *Candida auris* (*C. auris*) in a clinical specimen by the detection method of the present invention.

The results are shown in FIG. 2.

As shown in FIG. 2, the amplification product produced by the LAMP method from the clinical specimen was detected in 27 minutes. It was confirmed that the LAMP method using the LAMP Auris primer set was applicable to a clinical specimen directly. The whole identification process including the direct extraction of DNA (i.e., extraction without disruption) was completed within about 1 hour, and it was confirmed that rapid detection could be achieved.

<Example 5> Detection of Candida auris (C. auris) in Environmental Sample by LAMP Method The applicability of the LAMP method using the LAMP primer set to an environmental research was also evaluated. About 25 µL of physiological saline containing $1 \times 10^6$ cells of Candida auris (C. auris) was dried in a clean petri dish, and the cells were collected by a wiping method that had been optimized for environmental sampling use (samples A to D).

The cell amounts and the collection rates of samples A to D are shown in Table 3.

TABLE 3

| Sample | Amount of collected cells (cells/µL) | Collection rate (%) |
|---|---|---|
| A | $5 \times 10^2$ | 51 |
| B | $5.6 \times 10^2$ | 57 |
| C | $6.25 \times 10^2$ | 63 |
| D | $3.75 \times 10^2$ | 38 |

The handling of swabs and the extraction of DNA, excluding the shaking, were carried out in the same manner as in Examples 2 and 4. With respect to samples A and B, a vibration shaker was not use. With respect to samples C and D, the vibration shaker was used for 10 minutes. The reaction conditions for the nucleic acid amplification reaction by the LAMP method and the detection of an amplification product were the same as those employed in Examples 2 and 4.

Figure 3:
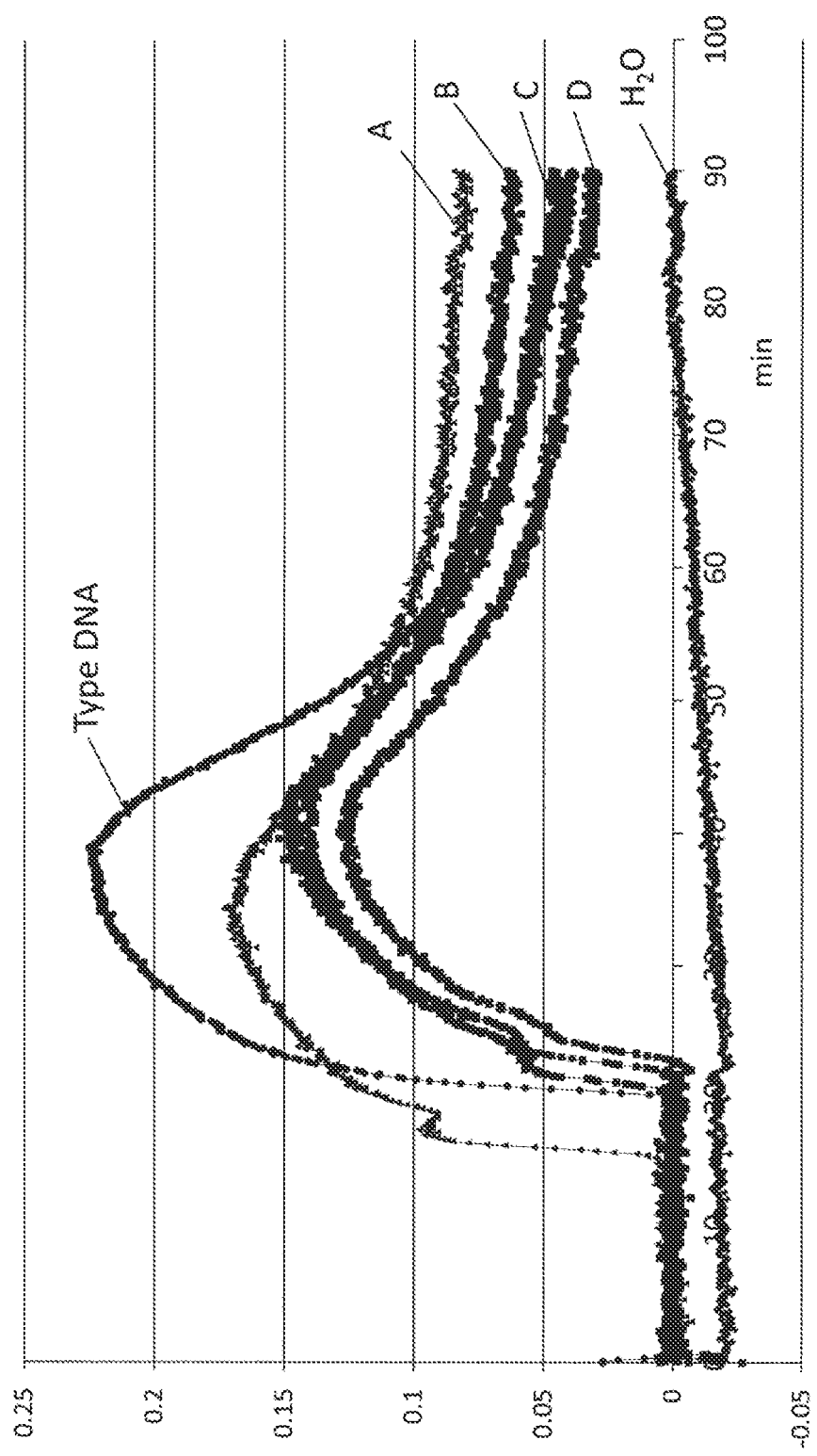
FIG. 3 is a diagram showing the results of the detection of *Candida auris* (*C. auris*) in an environmental sample by the detection method of the present invention.

The LAMP reaction times and the detection results for the samples are shown in Table 4 and FIG. 3.

TABLE 4

| Specimen No. | Specimen | Time required until LAMP auris-positive reaction occurs (min) |
|---|---|---|
| 1 | Distilled water (negative control) | Positive reaction does not occur |
| 2 | Sample A | 21 |
| 3 | Sample B | 16 |
| 4 | Sample C | 22 |
| 5 | Sample D | 23 |
| 6 | Candida auris DNA (positive control) | 20 |

As shown in Table 4 and FIG. 3, with respect to each of the samples (A to D, positive control), an amplification product was detected (LAMP-positive) 20 minutes after the start of the nucleic acid amplification reaction by the LAMP method, and it was confirmed that Candida auris (C. auris) DNA was detected. It was suggested that the LAMP method using the LAMP Auris primer set was applicable to environmental researches and enabled rapid and accurate detection.

From the results of Examples mentioned above, it was confirmed that, according to the LAMP method using the LAMP Auris primer set, all of C. auris strains were able to be identified with 100% of specificity and were able to be detected distinctively from closely related species thereof with high reliability. Furthermore, the target DNA was detected at a concentration of $2 \times 10^1$ copies per reaction, and therefore there was no technical problem about the use of an amplification device and the results were obtained within a short time. Furthermore, it was also confirmed that the detection from a clinical specimen was possible and therefore the time necessary for culturing or extraction of DNA was shortened, and early diagnosis became possible. In recent years, a portable LAMP amplification device and the like are commercially available. Therefore, according to the LAMP method using the LAMP Auris primer set of the present invention, the rapid and accurate detection of Candida auris (C. auris) becomes possible in, for example, environmental researches in medical facilities where the environmental control is critical.

The invention claimed is:

1. A primer set for detecting *Candida auris* by amplifying a *Candida* auris target sequence in a specimen by the loop-mediated isothermal amplification (LAMP) method, comprising a forward inner primer (FIP), a backward inner primer (BIP), a forward outer primer (F3) and a backward outer primer (B3), wherein:
FIP is a polynucleotide comprising SEQ ID NO: 1;
BIP is a polynucleotide comprising SEQ ID NO: 2;
F3 is a polynucleotide comprising SEQ ID NO: 3; and
B3 is a polynucleotide comprising SEQ ID NO: 4.

2. The primer set according to claim 1, further comprising polynucleotides respectively comprising SEQ ID NO: 5 and SEQ ID NO: 6 as loop primers.

3. A *Candida auris* detection kit comprising a primer set for detecting *Candida auris* as recited in claim 1.

4. A method for detecting *Candida auris* comprising:
a) contacting a nucleic acid sample obtained from a specimen with the primer set as recited in claim 1;
b) subjecting said contacted sample from step a) to loop-mediated isothermal amplification; and
c) detecting an amplification product.

5. The method for detecting *Candida auris* according to claim 4, further comprising polynucleotides respectively comprising SEQ ID NO: 5 and SEQ ID NO: 6 as loop primers.

6. A *Candida auris* detection kit comprising a primer set for detecting *Candida auris* as recited in claim 2.

\* \* \* \* \*

SEQUENCE LISTING

<160> NUMBER OF SEQ ID NOS: 16

<210> SEQ ID NO 1
<211> LENGTH: 42
<212> TYPE: DNA
<213> ORGANISM: Artificial Sequence
<220> FEATURE:
<223> OTHER INFORMATION: FIP primer

<400> SEQUENCE: 1
aggctactga gcttgctggt gtaaccaaac caacaggaga gg           42

<210> SEQ ID NO 2
<211> LENGTH: 42
<212> TYPE: DNA
<213> ORGANISM: Artificial Sequence
<220> FEATURE:
<223> OTHER INFORMATION: BIP primer

<400> SEQUENCE: 2
acggtttcag ggttagcatg gctcaacaaa gtcgctggta ca           42

<210> SEQ ID NO 3
<211> LENGTH: 19
<212> TYPE: DNA
<213> ORGANISM: Artificial Sequence
<220> FEATURE:
<223> OTHER INFORMATION: F3 primer

<400> SEQUENCE: 3
gggaaaggaa ccctgacct                                     19

<210> SEQ ID NO 4
<211> LENGTH: 20
<212> TYPE: DNA
<213> ORGANISM: Artificial Sequence
<220> FEATURE:
<223> OTHER INFORMATION: B3 primer

<400> SEQUENCE: 4
ggacacagca ttcgaagtgt                                    20

<210> SEQ ID NO 5
<211> LENGTH: 18
<212> TYPE: DNA
<213> ORGANISM: Artificial Sequence
<220> FEATURE:
<223> OTHER INFORMATION: Loop-F primer

<400> SEQUENCE: 5
catctcgaag gcctcggt                                      18

<210> SEQ ID NO 6
<211> LENGTH: 19
<212> TYPE: DNA
<213> ORGANISM: Artificial Sequence
<220> FEATURE:
<223> OTHER INFORMATION: Loop-B primer

<400> SEQUENCE: 6
cacatactcg aacggagtc                                     19

<210> SEQ ID NO 7
<211> LENGTH: 872
<212> TYPE: DNA
<213> ORGANISM: Candida auris

<400> SEQUENCE: 7

```
cactacagca ggatcaacgg atgcttcata ctctgaaatc acctttaatg ctgggattgg      60
cgcccacaca aagttggctg ggtggacaaa ctcctccaca gaaacagaac cgaaacggcc     120
agcgaggaac aacgaagcag caacgtcagc cttcaaggtt gagccagcat ccgaagatac     180
cacaacaacc ttgcgtgcag acgaaggcac agaagccacg aagtgttctt gagcaaatgg     240
gaaaggaacc ctgaccttaa ccaaaccaac aggagaggaa accgaggcct ggagatgac      300
accagcaagc tcagtagcct ggtgagcacc aaaagcgaca aaaacagttt cagggttagc     360
atggcccaca tactcgaacg gagtcaaatt tgtaccagcg actttgttga cacttcgaa      420
tgctgtgtcc actgcctttt ccaaagaata gtcgccgtcg ggaatcgaag acaccaattg     480
ctggtataag cggcccacat cggtcacaga caagatgtca tcgaacttgg agatcgcttt     540
agcaaactca ggaccgtcga aaacgtgcaa ggctggtccc tgaagcaaag tagccacaaa     600
gtgagtgaag atggtgatgt actgcaactc cacggcgctc tgcgagtccg ccggggccac     660
cacagggata cccgtggagc gagcagttgc caaaggagtc gtatagtttg aaaccaacga     720
gtttgtttcc acatcaaagt cgatagcgga aacgttcaag gtcaatggca attttgcagc     780
cttggccaaa gtgggctgca tccatggcaa ggcgttggcg cccaacacag cagtatgtgg     840
tccagtggag acacgttgc tagcggcata gc                                     872
```

<210> SEQ ID NO 8
<211> LENGTH: 1533
<212> TYPE: DNA
<213> ORGANISM: Candida auris

<400> SEQUENCE: 8

```
agtaagagct gcggtcatca agctcaacat cttcatcgtc tatcgccgac agagacgcct      60
ccatttggtt ttttcttgtt aaattgtcca ccgacaaagg ctggtggcct gaagtctccg     120
cagagtctgc cataaagttt gagcaattgt agatgttgta ggttttttt gcaagtgtta      180
tcggcgtccg aagttgaagt gtgacgggcg cgcaggaagg tcagaaagca gcaaggaaac     240
ggccaaaggt accagataga agaaacggtc tgttggggct gattttgtag aaactgatgt     300
ttaattcaca ttttcttcac ccgtgggggt tcgttgggaa ccgtcacgag gcacgtttgt     360
tgtgggcac gtgtggttgc aaaatgagat aagcaaggta gtgtggtttg acagcttcat      420
ataggaaggt gcaaaaaagt gcaaagagag aagaatgtaa attgaaattg taatattcca     480
atgagtgaag tgctaatttt ggaaatctga gcttttttaat gtctactcaa ctttgatgtt     540
tcagtggatg aagcctgttt ggcgtaaagt ccacaggttt tcggagtttt ggcgagcatc     600
gacacataac aaggcaacaa tgcaaagtca cgaaaatctc gaacaatggc gagtcgtaaa     660
ttgggtctct gattttccta gcgtgaattg aacagaaaca gtccaagtcc atgcttgcat     720
tcagtcactt gttttgagat gtggccggtg agagccactg aaagcgaacc acatacatgt     780
atccataatg tacacaataa aggctcctag atcaaaggat caagctcata atacaagcaa     840
caacgccatc gtgtcagccg agctatttga gtgtcacctg aagaataata cccatacttg     900
cgctcttaag tggtagtatc tgctgagcgt ctatctgatc tgttgaactg ctaccacgag     960
ctttggggat ttttcgcagc aattatacct gggcaaatac aaagcacaat attcacaagc    1020
acagcacttg taggcgacct catgccactg gtctgattaa caaacaataa gcttttgttt    1080
gataaaacta ataacggatc ttgcgagggt gatgtagcta tgaagaacat gcatgcaacc    1140
```

-continued

```
tcagccagca tgaggtatta gctcgtagaa tggctacgaa gagacctaaa caaaagtaga    1200
agtaagttta aagcctttcc gatggaattt aacaaactac aaagtggagc aattcttttt    1260
gtcggctgtt atctgcttga gtggtattca tcacgctgtc tgtgctcccg aggactctcc    1320
gataccacaa actataatgt taaatccaca tattttacat gagccgagat gaagttatgc    1380
agactcaaca caaaggaaat caggggtcgt atcttaagtt cttcttgttt ctaataatcc    1440
tctccagagg actccatttg cagccacaaa tacctcatcg cgaaaaagtg cagcttcatc    1500
tcactccata actatgtcag ctgccgtcga aac                                 1533

<210> SEQ ID NO 9
<211> LENGTH: 1924
<212> TYPE: DNA
<213> ORGANISM: Candida auris

<400> SEQUENCE: 9
atacttcaac gaaggagatt acttccaatt tcgaagcaaa agattggggt cagaagagcc      60
caagtcacca aggtcaggtt atgactcgac aaagcaagca acagccgacg aagataaatc     120
ggagggagat gaggacgata tattaaatga gggaaacctc catttccttg actttattga     180
gaataaaacc tttggtgtca accccagatc aaagtcggtc ttcgaccgcc tggcatacga     240
ctctgttgct ttcatgtcga acgatgctga ggaagaggaa aaggagaaat ctctcacgac     300
taccttagaa gttcttgttg ctccagattc tccgcctcca agcgattacg tgatcgatct     360
tattcacgag atatcatcaa tttgcacgga cgtaaaactc atgttacgtt cgctcaatgt     420
gaaacaaatg tcgaaagcgt tgaagcgac tgaggaggac taccacaagc ttgaaagttt     480
ggctcgtcaa gaacgtgaaa ccgacgaaga caacaatctg caaatcacta tgaaacagac     540
gtcacctact aggccatcgg tgacgacgct aaagacgggc agtggatctg tggcttctgt     600
tccgttcagg cgtctgcaaa cactggaaat cagtgagcag attccgccac cgtcgcaatt     660
gcaaggcatg agatcgtcaa catcgctcaa caccacaaca tcggctctca aattcacgcc     720
tcttaagtct gcaacaacag gtggtaaaac atttctaag ggcctgctcg aagacaacaa     780
agatttggac cggcgcattg cacaacttgt gaaagaagat gagaagaaga agctgaaggc     840
tgccaaagaa gagaagcaaa gattggcgaa agaagagaag ctagctgcta acaaagcaa     900 gcagagggaa aaggaaaaac aaagagagga gttgtcgcat acgaagcaca aggctactcc     960
tcttgaaagg aaccatactg agccacaaga cttcttctct acgaagctga accgcgaaga    1020
taccgatgag tcttcgttgt tttcgaagcc atcgatcact tcgaaagaca agaaggaag    1080 cattatactg cggatcggac acaaactcaa acataccgag ccgctcaagc acacggagtc    1140
tgttgacagt gatgtgagga gtatttccac aactaaatcg tccagtagcc aaacgtcaaa    1200
cactagcaag aagtcgtcac gcaaggttgg attatttggg ttgcgcaaga ggaattgaga    1260 aacaaaggc aagagagaaa aaaaaaaaa aaatatatat atatatacta gttggagga     1320 gaaatcaatc tgctccttgt cagtgtcttt tggaatgatt gcatcgtaat attctttct    1380 ggagattttt tttgggtttt ttggaacagc tgcaacacca tcaacactct gagaaacaac    1440
tccccgagac gcgccagctg cggctgccgc gtaggaaagt tgagcccac tggacttttg    1500 agaagtctgg gtgccggagg agggaccttc ggcgcgattt ggggaggaag caaccttagt    1560
tgctttctcc aggatcattg gatcgctgag cagggagttt ctgttctcct gacgcgtacc    1620
gccttctacg gatgcgacgc tagaagatac agaaacacct tttccaggac gatcaaactc    1680
gataggtggt tcaggaggtc gggaatctcg ctccacggta ccgggaggtc gattcgcgcc    1740
```

```
ttctgcttga tgccgaacga tattattcag cattttttcaa aaaggatcta agggtgtaag      1800
cttgagcttg taaatgtatt ctagaacacc gaagtattta aaactttgct ttgagtcttt      1860
tattgtatta ttaactactg tttactattg ctgtcatatt gaacaccttt ttgaaattcg      1920
ccac                                                                  1924
```

<210> SEQ ID NO 10
<211> LENGTH: 4646
<212> TYPE: DNA
<213> ORGANISM: Candida auris

<400> SEQUENCE: 10

```
cttcgttgcg ttgagaagcg ccttgtccaa cttttttggac tgctctaaaa agctgcgaag       60
cttcttagac ttggagtaaa cttgtaggaa tgacacggct acaccttgaa aagggtgat       120 ggggggagtg actcctccgt gaacgtagag catgtacatg aaagttgcgt agaggccacc      180
tttcgagccg gcaacaaaga tctcaaatac ttgtgtgtaa atgggcttgt tctcccacac      240
acgttctgaa acatcttcgt cgtcgggatc ctcgtcctca tcgctgattt cctcatcatt      300
cgatacctcg ttgccacccg gcgacagcaa tccctgatta ttggggatgg tgtagaacat      360
gagctcataa acgttgagta cgagtttacc gaagtatgct attgcttcca tcccgagcac      420
tccgtagtgg ataccaaaca agagactacc aacagaacgt gtgccctgga agacgtcgta      480
agccaaaaac ttcgctagga ggaggtcggc gacagtaaat acctcgagaa gaatcagaac      540
cctatacgtg gcgaagttgt agaagacctg gcgagaggtt gatatctgat gcggaatcat      600
gttcgtgatt ttcatctgaa acgagtcaag acggtccgtc atgatgatat gaaacacttt      660
gaacatgatc gtgaggttga tccacactat attgagaaga agattatcgt cactaaacat      720
gattatgaga agattaataa ggtagaaggg taactcctcc gaaatatgct caatttcaat      780
gatccgaagc tctctgaaga tcaattttgat ccctgcaaac cccatgagaa taaagcaact      840
taccacgaag ttgaggagaa ttaggagtct cacgctctcc gtgagctcgt acatcatggt      900
aagataatcg acagagttca tggccagaac cacgagcgat gcagcgaaaa ggccgaagct      960
aatgccgcca tacactgcaa ttgcaatggt gcccttttcga ggcatggtta tggtgttttg     1020
tctttctttt gtggggacga aaggtgtgga agccggaagt aaacacctca ccttcgcgat     1080
aatcctagat ctacgctaac ttgcgcatag agggtcgtgc gcgcaaaatt ttccccagac     1140
ttccaattag tggtcgcttg agtctattaa agttgcggaa ttcgggactt atggaggtca     1200
ttgcgtaatg gtgacatttc agttcgtctt cttttgatgt ctggaatcat gctctgtccg     1260
tttaattgcc tcataggcag cctcagtggc agtctcatgg gcagtcgcag aggtgatctg     1320
gatgctggta agttgccgg gcgcttcaat tgagcaggtg atctttgtag ctctgacaat     1380
gattgggaaa atattttgag gttcttctcg gtgtgattta agtcgcgaga aattccgtgg     1440
tagttcttat cgatcatgtc ggatacaata tgtgcctttt gagttgcagc tttctctata     1500
gagtccgcct ggctgcgact agtattggta atatcagcca aagcattatc ataacttgt     1560 ttggtctcct tctgtaatct tccaaaggct ccctgcacat ctttggtggc aacctctttg     1620
aaggacttga gatccgtggc cactgacttg gtctttgttg atatcgactg tagcgtttgg     1680 gaatttgat gaatgtaggc ctgatactct ttgcttagag ttgtcttctc ttcttgcatg     1740
aattctgttg cactttccct aaccgcctcg gcattgcgt ccttgcttga cttcacgaac     1800
ccgtcaaatg ctaggtgcat tgttgcata tattgctcct taagtgcctc atacgtctct     1860
```

```
gccatacgag ccttgaactt cttctcaaag gccttgtaca ttgcggagtc ttccagaaga      1920
tgtgttgagt tgatgtaatc cgttagttgc tcattcctct tgttcactcc agctacgtgc      1980
agcgagaaat cgaggttttg acaaacatta tgaagggtag aaaagtccat cagattagcg      2040
agaacctgct cgaaggctga tgtctccttc tctactttgg aagaaacatc atttaatttg      2100
ccctcgagag tcttcttaaa aaggcaaaga tgcgtttgaa cgacggtggg gatctccttc      2160
acattcagca gcacctgagt taggtcatta agattgttaa tcacctcatt aacgtcccta      2220
atgatactca gaattccagt cctgtaaca ttagagactc gctcttttg agagctgtat       2280 ttgtctttta aatgcatgaa ctcttttgta gtcttgtgaa gctcagcgtc tttagctgcg      2340
aggtccagcc tgcttttcga gttctcgcta agtgtttgct cgatctgtag tttgagttct      2400
gcaatatcct tgtccctccc ttgaagtttg gcgtgtagcc ctgtaatctg agtgtctttc      2460
tccttcaact cggttctaag ttccgcaatt ttcctttcaa agtcctcgta gttctgaaga      2520
ctgatcctga tgctgttgtc tttgcctttt gtagccaata agtctctatt caatctagaa      2580
atctccgctg ataactccct tatctttgta cgtttgagaa cgagctcgct gtcggccgtc      2640
gattgtggta tattttgat attcttcgcc ttggaagcgt aagttagcgt cagcatcgtt      2700
tccattaagt tcagctttgc cggggaaatg gtagcaatca atgcggtttt ggtccgccct      2760
ccaatagagc cttgaagaag acgggtgagt ttagactctc tataaggtat atgtctaggt      2820
tctttgcctt cactcaatgc actgatgacc tttcccaaag tcaaaagact ctggttgatc      2880
aggcccgctt ctttggcact agcatcggta gcgccagact tgatgatatc ttccagcccc      2940
gcgagatcca ccaaattcat ttttgacagc cgcaccacct cttgccctga cgacgacatt      3000
actgttttgt gaagcgttat ggtgaaaatg gtgtgagaac gtgatgagcg ggagttgagt      3060
ttagtggtac ccatcttcct cttccctagg cactttgta gcatctcaaa ccccagcttc       3120
gcatccacca cgtcaagctc atacaaattc tggatcattg ttccccttcc atctctcgaa      3180
ccatccccta ggagcttag tttcggcttt tttgagttca actcaagctc atcgttgacg       3240
agatcatgga gctcttcctt gtacaattcc acacacgaca acttgacaca gatgtcgtct      3300
ttggccacct gaaaaagctc ttgcaacaca cgaggcacaa tacccgcatg ctctcccact      3360
aaatccccca acattgtata cgtctttcct gagcctgtca ggccatacgc aaggatagtg      3420
acattcatgc ctgccatgaa atctcgaagt aacggacgag caatgttttt gtaaatgagt      3480
tcctgatcag cattggcacc atagacttgg tctagtgtaa atactttgcc tgaaccgtct      3540
gatccagagc caaaggaagt gttgggggaa gcattcacgc taacgtaggg ttcatccgtg      3600
gaacagaaat cgtcaggcac cgagaccaca atcggggact gggcggctat ctccagctca      3660
gttcttcttc gcacacgggc gctgacctgg attttgtcgg acatatagta cagttttttt      3720
tttgtagtct ttctttgtgg agattatggt gatgtttatg tttgtttacg atgggcggcc      3780
tgtgtgcagg tcggaacggt caaagcatgt agagtgtcta gagtctttat cgatgaatgg      3840
aagtagagga ggtaaaattc taatagtgag attctttttt cgatggacgt gttttttgttt     3900 acgttcctcg tacttagtta tgtttcgggt ttaatggtgt ttagtgagaa atggctgcaa      3960
aatgcaaaat gctgcgaaaa agtatagatc agagaaagac aatactactg tctgataaaa      4020
aacaaaagtt gatgataaga ataccagaat ttgtactcac atataggaaa tcacctagag      4080
tttgatatat aatctgacac agcaatgtca aaatcgcttt taccacgtgc tataaaaagt      4140
ttctaaggac gtcaccttct cgatataaga taagcattct gtgaacggct gttaggaaag      4200
agcatagtga ggtatttcag ttgaaatacg tatgccaaaa aaaaggcaac cattaattag      4260
```

```
attccacgtg gttcactaca ctgaaaacag atgaactgtc tacaatacag tctgtcagtg    4320
caatgcctac cagttgctgg tggcatagca cctcacgaat ggatatattc gctaccaggt    4380
tttgtacagc tcaaaccact acatagctgg tttctgtcaa cctcgtcgct atcaactaac    4440
aaactctttt actaaaaaag agaagctctt ctttcactac acgtactgta ctagccttcg    4500
ctcgtgtgac gattagccag ccgtactttt ccccatcacc gtaaaccatc tattgatgtt    4560
catatataca gattccaatg acgacgccaa tggcaatgcc acgagccccc aaaaacctca    4620
atcaaagaaa tcatcgtcat cttcat                                         4646
```

<210> SEQ ID NO 11
<211> LENGTH: 18
<212> TYPE: DNA
<213> ORGANISM: Artificial Sequence
<220> FEATURE:
<223> OTHER INFORMATION: Auris F primer

<400> SEQUENCE: 11

```
gctatgccgc tagcaacg                                                  18
```

<210> SEQ ID NO 12
<211> LENGTH: 20
<212> TYPE: DNA
<213> ORGANISM: Artificial Sequence
<220> FEATURE:
<223> OTHER INFORMATION: Auris B primer

<400> SEQUENCE: 12

```
cactacagca ggatcaacgg                                                20
```

<210> SEQ ID NO 13
<211> LENGTH: 40
<212> TYPE: DNA
<213> ORGANISM: Artificial Sequence
<220> FEATURE:
<223> OTHER INFORMATION: FIP primer

<400> SEQUENCE: 13

```
gtggtatctt cggatgctgg ctccagcgag gaacaacgaa                          40
```

<210> SEQ ID NO 14
<211> LENGTH: 40
<212> TYPE: DNA
<213> ORGANISM: Artificial Sequence
<220> FEATURE:
<223> OTHER INFORMATION: BIP primer

<400> SEQUENCE: 14

```
acaaccttgc gtgcagacga agggttcctt tcccatttgc                          40
```

<210> SEQ ID NO 15
<211> LENGTH: 19
<212> TYPE: DNA
<213> ORGANISM: Artificial Sequence
<220> FEATURE:
<223> OTHER INFORMATION: F3 primer

<400> SEQUENCE: 15

```
agaaacggaa ccgaaacgg                                                 19
```

<210> SEQ ID NO 16
<211> LENGTH: 20
<212> TYPE: DNA

```
<213> ORGANISM: Artificial Sequence
<220> FEATURE:
<223> OTHER INFORMATION: B3 primer

<400> SEQUENCE: 16
cctctcctgt tggtttggtt                                              20
```